United States Patent [19]

Frachet et al.

[11] Patent Number: 4,923,469
[45] Date of Patent: May 8, 1990

[54] PROTHESIS AND ELECTRODE FOR THE ELECTRICAL STIMULATION OF THE INNER EAR, AND METHOD FOR PRODUCING SAID ELECTRODE

[75] Inventors: Bruno Frachet, Montmorency; Michel-Yves David, Paris, both of France

[73] Assignees: Assistance Publique; Audit S.A., both of Paris, France

[21] Appl. No.: 178,345

[22] Filed: Apr. 6, 1988

[30] Foreign Application Priority Data

Apr. 6, 1987 [FR] France ................................. 87 04832

[51] Int. Cl.$^5$ ................................................ A61F 2/18
[52] U.S. Cl. ........................................ 623/10; 128/642; 128/784; 128/420.5; 128/420.6
[58] Field of Search ................. 623/10; 128/642, 784, 128/789, 420.5, 420.6, 784, 419 P; 381/68

[56] References Cited

U.S. PATENT DOCUMENTS

| | | | |
|---|---|---|---|
| 3,196,462 | 7/1965 | Robinson | 623/10 |
| 4,052,754 | 10/1977 | Homsy | 623/10 |
| 4,292,693 | 10/1981 | Shea et al. | 623/10 |
| 4,440,178 | 4/1984 | Bussard et al. | 128/419 P |
| 4,606,329 | 8/1986 | Hough | 600/25 |
| 4,622,975 | 11/1986 | Danby et al. | 128/642 |
| 4,655,776 | 4/1987 | Lesinski | 623/10 |
| 4,781,196 | 11/1988 | Killion | 128/642 |

FOREIGN PATENT DOCUMENTS

| | | |
|---|---|---|
| 2068 | 5/1979 | European Pat. Off. . |
| 2465474 | 3/1981 | France . |

Primary Examiner—Richard J. Apley
Assistant Examiner—Stephanie L. Iantorno
Attorney, Agent, or Firm—Wenderoth, Lind & Ponack

[57] ABSTRACT

A prosthesis permits both an acoustic stimulation and an electrical stimulation of the inner ear and include an interposition element, one end of which is provided with a device for attachment to a downwardly extending branch of the anvil. The other end of the element is adapted to be applied on the oval window of the ear and has a conductive end surface constituting an electrode which is connected by a conductor covered with a biocompatible insulating covering to a source of electrical stimulation.

3 Claims, 2 Drawing Sheets

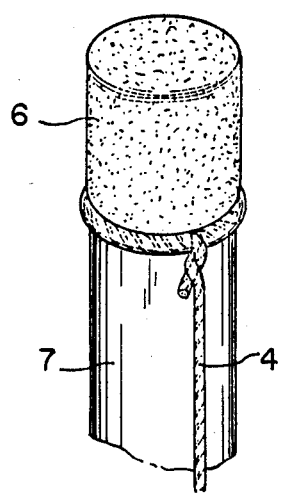
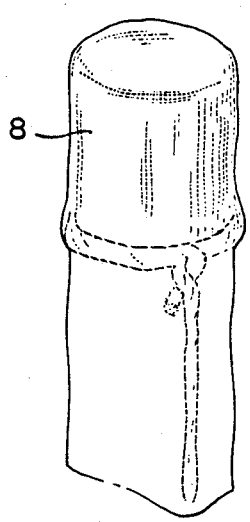
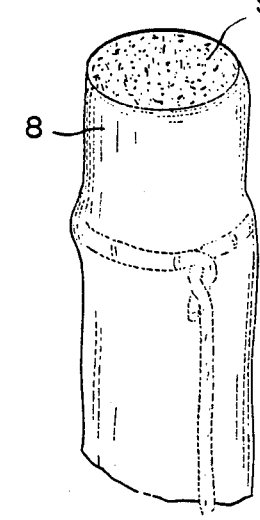
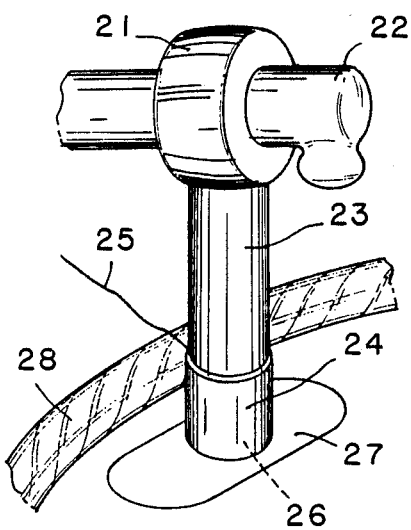
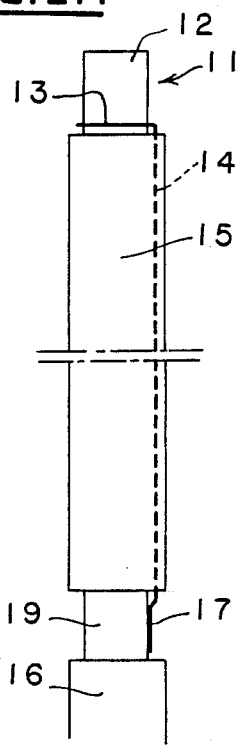
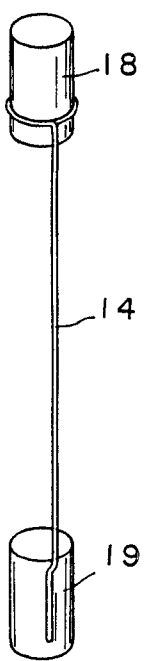

PROTHESIS AND ELECTRODE FOR THE ELECTRICAL STIMULATION OF THE INNER EAR, AND METHOD FOR PRODUCING SAID ELECTRODE

BACKGROUND OF THE INVENTION

The present invention relates to a prosthesis permitting both an acoustic stimulation and an electric stimulation of the inner ear in the case of complete neuro-sensorial deafness.

A number of techniques have already been proposed for producing electric stimulations of the inner ear, and in particular co-called "membranous" techniques in which an electrode is applied on the round window of the inner ear.

Such an electrode is secured by various methods employing in particular a biological glue, a resorbable spungy product, or fragments of muscular tissues. This manner of fixing is never exempt from displacement so that there is a considerable risk of ineffectiveness of the implanted device.

It should be added that anatomical variations of the round window often require adaptations of the surgical technique.

SUMMARY OF THE INVENTION

An object of the invention is to provide an auditory prosthesis capable of stimulating the inner ear through the oval window thereof.

Another object of the invention is to permit, in a particular case, the transformation of a conventional stapedio-vestibular prosthesis by fixing an electrode to an end of such prosthesis. It will be recalled that stapedio-vestibular prostheses are employed in the case of transmission deafness related in particular to an autospongiosis where the stirrup is replaced by an interposed element one of the ends of which is fixed to the anvil whereas the other end is applied against the oval window.

The invention therefore provides a prosthesis permitting both an acoustic stimulation and an electric stimulation of the inner ear, said prosthesis comprising an interposed element one of the ends of which is provided with means for fixing to the descending branch of the anvil whereas the other end, which is adapted to be applied on the oval window, is provided with a conductive end surface constituting an electrode which is connected through a conductor covered with a biocompatible insulating covering to a source of an electric stimulation.

In a preferred embodiment of the invention, the electrode is constituted by a metal cup in which the end of the interposed element is inserted and whose peripheral surface is covered by a biocompatible insulating covering, said cup being welded to the conductor.

The invention also provides an electrode for electrically stimulating the inner ear adapted in particular to be applied to one of the ends of a conventional stapedio-vestibular prosthesis, said electrode being constituted by a cup whose having an outer cylindrical surface covered with a biocompatible insulating covering, said cup being welded to a conductor covered with a biocompatible insulating cover.

Note that in neurosensorial deafnesses, usually the tympano-ossicular system and the mechanical system of the inner ear are normal. Thus it is possible to obtain with the prosthesis according to the invention both an acoustic stimulation producing the usual mechanical phenomena in the inner ear and an electrical stimulation of the nerve ends. In this case, the acoustic vibration is not perceived as a sound. In order to amplify this mechanical stimulation, a conventional auditory prosthesis may be disposed in the outer auditory duct.

The invention may be produced by a method including:

(a) producing a metal die having the diameter of the interposition element on which the electrode will be fixed, (b) covering the die with an insulation except for an end zone, (c) applying against the uncovered end zone of the die the end of a biocompatible and non-oxidizable metal wire, (d) forming by electrolytic deposition a biocompatible and non-oxidizable metal deposit on the uncovered zone of the die so as to form a biocompatible and non-oxidizable metal cup connected to the end of the biocompatible and non-oxidizable metal wire, (e) chemically eliminating the metal die, and (f) covering an outer cylindrical surface of the biocompatible and non-oxidizable metal cup and the biocompatible and non-oxidizable metal wire with a biocompatable and non-oxidizable insulating covering.

In the aforementioned method, biocompatible and non-oxidizable metal is intended to mean a biocompatible metal which is not oxidized in the stage (e) of the method, and preferably includes gold. Other metals such as platinum and iridium may also be used.

In stage (f) the whole of the outer surface of the cup is preferably covered with a biocompatible insulating covering and the end of the covering of the cup is cut off when it is used.

BRIEF DESCRIPTION OF THE DRAWINGS

The invention will be described in more detail hereinafter with reference to the accompanying drawings, in which:

FIGS. 1A to 1H are perspective views representing the different stages of the the different stages of the production of an electrode according to the invention;

FIGS. 2A and 2B respectively are an elevation view and a perspective view representing the different stages of the the different stages of the fixing of a terminal to the end of the conductor of the electrode; and FIG. 3 is a perspective view of a prosthesis according to the invention after implantation.

DETAILED DESCRIPTION OF THE INVENTION

FIGS. 1A to 1H represent the different stages of the production of an electrode according to the invention adapted to be applied to the end of an interposition element, in particular of a piston of teflon conventionally employed in a stapedio-vestibular prosthesis.

In the first stage of the method, a metal cylindrical die 1 is produced which has a diameter identical to that of the piston provided for placing the electrode in position. This die is subjected to boring, shaving, and polishing operations imparting thereto the desired shape and size and a shiny aspect.

Figure 1A:
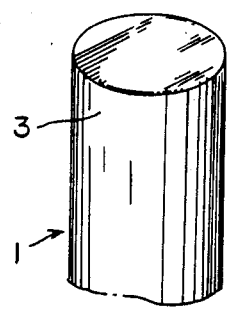
Figure 1B:
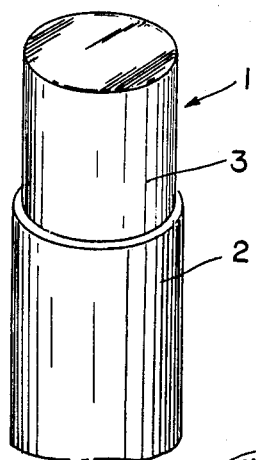

As shown in FIG. 1B, in the second stage of the method, a part of the die to be spared treatment when subsequently carrying out electroforming is protected with a layer of varnish and a silicone tube 2 while leaving bare only the end 3 of the cylindrical die.

Figure 1C:
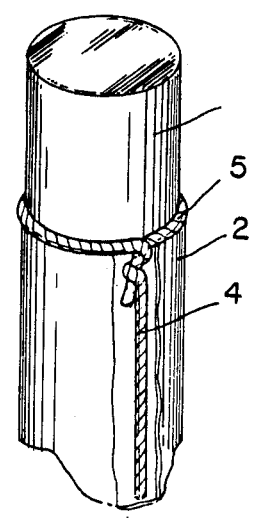

A wire of soft gold is produced from several strands each having 1 for example a diameter of 25 microns which strands are twisted together. This flexible wire is required for maintaining the mobility of the piston to which the electrode will be attached. This gold wire 4 is then threaded under the silicone tube 2 and its end 5 is applied against or around the end 3 of the die 1 so as to form, for example, a loop around end 3, as represented in FIG. 1C.

Figure 1D:
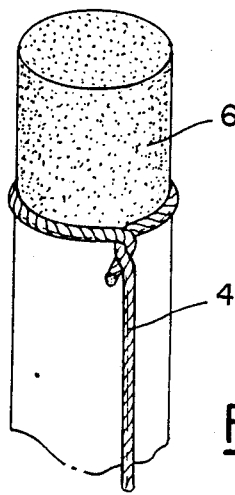

The assembly is then subjected to an electroforming by electrolytic deposition in a bath of non-toxic gold salt. The electolytic deposition is carried out, for example until a deposit of several tens of microns is obtained, which provides sufficient rigidity and a sufficient electrolytic weld. As shown in FIG. 1D, this deposit forms a cup 6 covering the end 3 of the die 1. During the electrolytic deposition, the end 5 of the gold wire is welded to the cup 6. The method described enables the thickness of the deposit to be reduced to a low value since the hardness of the deposited gold is about 250 Vickers. It is advantageous to reduce as far as possible the thickness so that the total diameter of the electrode is of small value and does not, when placed in position, come into contact with the facial nerve which is close to the oval window.

Figure 1E:
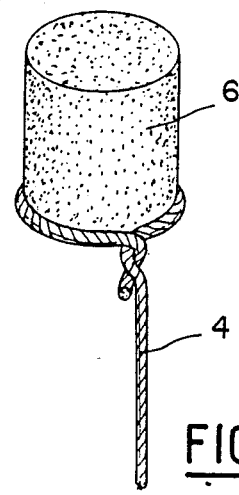

The metal die is thereafter eliminated chemically by plunging the whole of the cup/gold wire, die assembly into sulphuric acid or any other acid permitting the dissolving of the die. In this way there is obtained cup 6 to which the gold wire is fixed, as shown in FIG. 1E.

As represented in FIG. 1F, a teflon piston 7 is then inserted in the cup 6, this piston having such diameter that it is introduced with friction so that it cannot leave the cup when the assembly is placed in position.

The assembly comprising the cup 6 and the wire 4 is then immersed in a bath of adhesive biocompatible silicone dissolved in trichlorethylene, several times so as to obtain by successive capillary deposits, a total covering 8 having sufficient thickness, as shown in FIG. 1G. The assembly is then left in the open air for 24 hours until complete polymerization and elimination of any trace of solvent.

The electrode is now ready for implantation. It is sufficient during such operation to cut off the end of the silicone covering 8 so as to bare the planar surface 9 of gold which constitutes the electrical stimulation electrode, as shown in FIG. 1H.

In the manner according to the invention, a connecting terminal as shown in FIGS. 2A and FIGS. 2B may be at the same time produced. For this purpose, there is employed a die 11 of great length and having a end 12 surrounded by the end 13 of a gold wire 14. The assembly of the die 12 and gold wire 14 is surrounded by an insulating sleeve 15 which is interrupted in the vicinity of the other end of the die 11 so as to leave bare a part 16 of the die and a part 17 of the gold wire.

The assembly is then subjected, as before, to electroforming by electrolytic deposition in a bath of gold salt so as to deposit the gold on both the end 12 of the die 11 and the part 16 of the latter. After disassembly and chemical elimination of the die, a gold cup 18 connected by the wire 14 to a gold terminal 19 is obtained.

The assembly, after protection of the inner parts, is then covered externally with a biocompatible insulating covering.

FIG. 3 shows a prosthesis according to the invention after it has been placed in position. In the course of an operation, the stirrup is removed and the prosthesis according to the invention is fixed in lieu thereof.

The prosthesis comprises a fixing head 21 which surrounds the downwardly extending branch of the anvil 22. This fixing head 21 is connected to a teflon piston 23 at the end of which is fixed an electrode 24 according to the invention, connected by a gold wire 25 to a supply. The end 26 which constitutes the electrode proper is in contact with the membrane 27 of the oval window, or a tissue such as a vein graft is inserted therebetween.

As can be seen in FIG. 3, the diameter of the electrode must be small enough to avoid any contact with the facial nerve 28. Another electrode or a reference electrode is implanted in the neighbouring tissues.

It will be clear that the interposition element may not only be made from teflon, but from any other material which is biocompatible and conductive and which may be easily cut during an operation for adapting it to the patient.

The prosthesis according to the invention not only may be employed in the case of complete neurosensorial deafness but also in the treatment of tinnitus and buzzing.

We claim:

1. A prosthesis capable of achieving both an acoustic stimulation and an electrical stimulation of the inner ear, said prosthesis comprising:
   an interposition element having first and second ends and means provided at said first end for fixing said interposition element to the descending branch of the anvil of the ear, whereby acoustic stimulation may be transmitted through said interposition element;
   means forming a conductive end surface and defining an electrode on said second end for application against the oval window of the ear, said electrode comprising a metal cup within which is inserted said second end of said interposition element, said metal cup defining said end surface and having an outer cylindrical surface;
   a conductor welded to said cup of said electrode for connection to a source of electrical stimulation;
   a biocompatible insulating covering covering said conductor; and
   a biocompatible insulating covering covering said outer cylindrical surface.

2. A prosthesis according to claim 1, wherein said cup and said conductor are composed of gold.

3. A prosthesis according to claim 2, wherein said conductor is formed by twisted gold wires.

* * * * *